(12) United States Patent
Huang et al.

(10) Patent No.: US 10,197,534 B2
(45) Date of Patent: Feb. 5, 2019

(54) METHOD AND DEVICE FOR TESTING DEFECT BASED ON ULTRASONIC LAMB WAVE TOMOGRAPHY

(71) Applicant: Tsinghua University, Beijing (CN)

(72) Inventors: Songling Huang, Beijing (CN); Shen Wang, Beijing (CN); Wei Zhao, Beijing (CN); Shisong Li, Beijing (CN); Zheng Wei, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 407 days.

(21) Appl. No.: 14/948,398

(22) Filed: Nov. 23, 2015

(65) Prior Publication Data

US 2016/0146762 A1 May 26, 2016

(51) Int. Cl.
*G01N 29/06* (2006.01)
*G01N 29/07* (2006.01)
*G01N 29/24* (2006.01)

(52) U.S. Cl.
CPC ....... *G01N 29/069* (2013.01); *G01N 29/0672* (2013.01); *G01N 29/07* (2013.01); *G01N 29/2412* (2013.01); *G01N 2291/0427* (2013.01)

(58) Field of Classification Search
CPC ............... G01N 29/0672; G01N 29/07; G01N 29/2412; G01N 2291/0427

USPC .......................................................... 73/598
See application file for complete search history.

(56) References Cited

U.S. PATENT DOCUMENTS

| 6,128,092 | A | * | 10/2000 | Levesque | G01N 29/069 |
| | | | | | 356/451 |
| 2005/0075846 | A1 | * | 4/2005 | Kim | G01H 9/004 |
| | | | | | 703/1 |
| 2008/0289423 | A1 | * | 11/2008 | Gordon | G01N 29/069 |
| | | | | | 73/602 |
| 2014/0211588 | A1 | * | 7/2014 | Falter | G01S 15/897 |
| | | | | | 367/8 |
| 2017/0191966 | A1 | * | 7/2017 | Niri | G01N 29/07 |

\* cited by examiner

*Primary Examiner* — Max Noori
(74) *Attorney, Agent, or Firm* — Houtteman Law LLC

(57) ABSTRACT

Disclosed are a method and a device for testing a defect based on an ultrasonic Lamb wave tomography. The method includes: partitioning an imaging area of a material to be tested into grids; exciting electromagnetic acoustic transducers for emitting to emit Lamb waves with a A0 mode in all directions, and electromagnetic acoustic transducers for receiving to receive the Lamb waves; obtaining a time-frequency analysis result and recording time-of-flights of testing waves; determining a first slowness of each grid to obtain a first defect area; establishing an extrapolation formula according to the first defect area, and iterating the extrapolation formula to trace and revise paths of the Lamb waves until a better imaging precision is obtained.

10 Claims, 3 Drawing Sheets

METHOD AND DEVICE FOR TESTING DEFECT BASED ON ULTRASONIC LAMB WAVE TOMOGRAPHY

CROSS REFERENCE TO RELATED APPLICATION

This application claims priority to and benefits of Chinese Patent Application No. 201410683016.7, filed with State Intellectual Property Office on Nov. 25, 2014, the entire contents of which are incorporated herein by reference.

FIELD

The present disclosure relates to a non-destructive testing field, and more particularly, to a method and a device for testing a defect based on an ultrasonic Lamb wave tomography.

BACKGROUND

Information of a profile and a size of a defect may be quickly and effectively obtained by using an ultrasonic Lamb wave tomography. A Lamb wave time-of-flight cross-hole tomography may perform a fan-beam projection and imaging by means of a linear transducer array, which is an iteration-based effective and quick tomography. The traditional Lamb wave time-of-flight cross-hole tomography is based on a straight ray theory, i.e., assuming that the Lamb wave travels in straight lines after encountering a defect in a propagation process. However, the propagation direction of the Lamb wave is deflected if a plate has a strong scattering defect. That is, the Lamb wave travels in curve. At this time, the straight ray theory is inapplicable, and the precision of the tomography is decreased. The above problem is a bottleneck confining the development of the Lamb wave time-of-flight cross-hole tomography.

SUMMARY

A first aspect of embodiments of the present disclosure is to provide a method for testing a defect based on an ultrasonic Lamb wave tomography. The method includes following acts performed by a computer: S1, selecting an imaging area on a material to be tested, and partitioning the imaging area into $N_1 \times N_2$ grids, wherein M electromagnetic acoustic transducers for emitting are set on a first side of the imaging area, M electromagnetic acoustic transducers for receiving are set respectively opposite to the M electromagnetic acoustic transducers for emitting on a second side of the imaging area, and $N_1$, $N_2$, M are positive integers; S2, exciting the M electromagnetic acoustic transducers for emitting to emit Lamb waves with a A0 mode in all directions and the M electromagnetic acoustic transducers for receiving to receive the Lamb waves successively, such that M×M testing waves corresponding to M×M Lamb waves are obtained; S3, performing a time-frequency analysis and a mode recognition on the M×M testing waves, so as to obtain time-of-flights of the M×M Lamb waves; S4, recording the time-of-flights of the M×M Lamb waves; S5, determining a first slowness of each grid according to the time-of-flights and a size of each grid to obtain a first defect area; S6, establishing a three-dimensional Cartesian coordinate system in the imaging area, and defining an original emission angle; S7, for a path of a Lamb wave through the defect, obtaining a phase velocity $c_p$ at a point P(x,y) on a forward direction of the Lamb wave through the defect and calculating $\partial c_p/\partial x$ and $\partial c_p/\partial y$ according to the phase velocity $c_p$, where x is a coordinate value of the point P(x,y) in a x-direction, y is a coordinate value of the point P(x,y) in a y-direction; S8, calculating an extrapolation point of the Lamb wave through the defect by introducing $c_p$, $\partial c_p/\partial x$ and $\partial c_p/\partial y$ into an extrapolation formula; S9, judging whether a coordinate value of the extrapolation point reaches or exceeds boundary coordinates of a corresponding grid, if no, using the extrapolation point of the Lamb wave through the defect as a new point on the forward direction of the Lamb wave through the defect and executing steps S6-S9, if yes, recording the coordinate value of the extrapolation point as a coordinate value of an end point of the Lamb wave through the defect; S10, judging whether the coordinate value of the end point of the Lamb wave through the defect reaches or is close to the electromagnetic acoustic transducers for receiving, if yes, obtaining a path with a shortest time-of-flight of the Lamb wave through the defect, if no, changing the original emission angle and executing steps S6-S10 until the path with the shortest time-of-flight of the Lamb wave through the first defect area is found; S11, obtaining a second slowness of each grid according to the time-frequency analysis result and the shortest time-of-flight and a change of a slowness curve in the defect to obtain a second defect area and to determine a size and a distribution of the second defect area.

In some embodiments, a diameter of the electromagnetic acoustic transducer is within a range of 20 mm to 80 mm, a distance between centers of each two adjacent electromagnetic acoustic transducers at the same side is within a range of 20 mm to 100 mm.

In some embodiments, the M electromagnetic acoustic transducers for emitting are excited by a radio frequency power amplifier, in which an excitation frequency of the radio frequency power amplifier is within a range of 50 kHz to 500 kHz.

In some embodiments, the Lamb wave emitted by the electromagnetic acoustic transducer for emitting is a Lamb wave with a single A0 mode.

In some embodiments, the first or the second slowness of each grid is determined according to formula (1):

$$T_i = \sum_{j=1}^{n} L_{ij} * S_j, (i = 1, 2, \ldots, m), \quad (1)$$

where $S_j$ is a slowness of a $j^{th}$ grid, $L_{ij}$ is a length of a $i^{th}$ Lamb wave in the $j^{th}$ grid, $T_i$ is a time-of-flight of the $i^{th}$ Lamb wave, $n=N_1 \times N_2$, and $m=M \times M$.

In some embodiments, the original emission angle is within a range of 0~180°.

In some embodiments, obtaining a phase velocity $c_p$ at a point P(x,y) on a forward direction of the Lamb wave through the defect and calculating $\partial c_p/\partial x$ and $\partial c_p/\partial y$ according to the phase velocity $c_p$ includes:

obtaining 16 pixels with the extradition point used as a center;

obtaining 16 phase velocities corresponding to the 16 pixels;

introducing the 16 phase velocities respectively into a formula (2) to perform a two-dimensional surface fitting on a distribution of the phase velocities:

$$c_p(x_p, y_p) = \sum_{k=0}^{3} \sum_{l=0}^{3} C_{kl} x_p^k y_p^l, \quad (2)$$

where $x_p$ is a coordinate value of a $p^{th}$ pixel in the x-direction, $y_p$ is a coordinate value of the $p^{th}$ pixel in the y-direction, $c_p(x_p,y_p)$ is a phase velocity corresponding to the $p^{th}$ pixel, $C_{kl}$ are coefficients to be solved, k=0, 1, 2, 3, l=0, 1, 2, 3, p is a positive integer and 1≤p≤16, such that $C_{kl}$ are obtained;

calculating $\partial c_p/\partial x$ and $\partial c_p/\partial y$ according to $C_{kl}$.

In some embodiments, the extrapolation formula is expressed as formula (3):

$$y_{k+1} = 2y_k - y_{k-1} + \frac{1}{c_p}\left(\frac{\partial c_p}{\partial x}\frac{(y_k - y_{k-1})}{\Delta x} - \frac{\partial c_p}{\partial y}\right)[(y_k - y_{k-1})^2 + (\Delta x)^2] \quad (3)$$

where $y_k$ is a coordinate value of a first discrete point on the Lamb wave through the defect in a y-direction at a $k^{th}$ step of extrapolation, $y_{k+1}$ is a coordinate value of a second discrete point succeeding the first discrete point on the Lamb wave through the defect in the y-direction at the $k^{th}$ step of extrapolation, $y_{k-1}$ is a coordinate value of a third discrete point preceding the first discrete point on the Lamb wave through the defect in the y-direction at the $k^{th}$ step of extrapolation, $\Delta x$ is a step size, and $\partial y/\partial x=(y_k-y_{k-1})/\Delta x$.

In some embodiments, changing the original emission angle includes: increasing or decreasing the original emission angle by 2~6°.

A second aspect of embodiments of the present disclosure is to provide a device for testing a defect based on an ultrasonic Lamb wave tomography. The device includes: a non-transitory computer-readable medium comprising computer-executable instructions stored thereon; and an instruction execution system, which is configured by the instructions to implement at least one of following modules:

a selecting and partitioning module, configured to select an imaging area on a material to be tested and partition the imaging area into $N_1 \times N_2$ grids, in which M electromagnetic acoustic transducers for emitting are set on a first side of the imaging area, M electromagnetic acoustic transducers for receiving are set respectively opposite to the M electromagnetic acoustic transducers for emitting on a second side of the imaging area, and $N_1$, $N_2$, M are positive integers;

an exciting module, configured to excite the M electromagnetic acoustic transducers for emitting to emit Lamb waves with a A0 mode in all directions and the M electromagnetic acoustic transducers for receiving to receive the Lamb waves successively, such that M×M testing waves are obtained;

a performing module, configured to perform a time-frequency analysis and a mode recognition on the M×M testing waves, so as to obtain time-of-flights of the M×M Lamb waves;

a recording module, configured to record the time-of-flights of the M×M Lamb waves;

a determining module, configured to determine a first slowness of each grid according to the time-of-flights and a size of each grid to obtain a first defect area;

an establishing module, configured to establish a three-dimensional Cartesian coordinate system in the imaging area and define an original emission angle;

a first obtaining module, for a path of a Lamb wave through the defect, configured to obtain a phase velocity $c_p$ at a point P(x,y) on a forward direction of the path of the Lamb wave through the defect, and calculate $\partial c_p/\partial x$ and $\partial c_p/\partial y$ according to the phase velocity $c_p$, where x is a coordinate value of the point P(x,y) in a x-direction, y is a coordinate value of the point P(x,y) in a y-direction;

a calculating module, configured to calculate an extrapolation point of the Lamb wave through the defect by introducing $c_p$, $\partial c_p/\partial x$ and $\partial c_p/\partial y$ into an extrapolation formula;

a first judging module, configured to judge whether a coordinate value of the extrapolation point reaches or exceeds boundary coordinates of a corresponding grid, if no, use the extrapolation point of the Lamb wave through the defect as a new point on the forward direction of the Lamb wave through the defect and make the establishing module, the first obtaining module, the calculating module and the first judging module to work again, and if yes, record the coordinate value of the extrapolation point as a coordinate value of an end point of the Lamb wave through the defect;

a second judging module, configured to judge whether the coordinate value of the end point of the Lamb wave through the defect reaches or is close to the electromagnetic acoustic transducers for receiving, if yes, obtain a path with a shortest time-of-flight of the Lamb wave through the defect, and if no, change the original emission angle and make the establishing module, the first obtaining module, the calculating module, the first judging module and the second judging module to work together until the path with the shortest time-of-flight of the Lamb wave through the first defect area is found;

a second obtaining module, configured to obtain a second slowness of each grid according to the time-frequency analysis result and the shortest time-of-flights and a change of a slowness curve in the defect to obtain a second defect area and to determine a size and a distribution of the second defect area.

A third aspect of embodiments of the present disclosure is to provide a non-transitory computer-readable storage medium having stored therein instructions that, when executed by a processor of a device, causes the device to perform a method for testing a defect based on an ultrasonic Lamb wave tomography according to the first aspect of embodiments of the present disclosure.

The technical solutions disclosed in the embodiments of the present disclosure may have advantages as follows.

In the present disclosure, the ray tracing (RT) iteration algorithm and the time-of-flight cross-hole tomography are combined to obtain advantages of the ray tracing iteration algorithm and the time-of-flight cross-hole tomography. By iterating, the paths of the Lamb waves may be revised to obtain the distribution of the defect. The technical solutions according to embodiments of the present disclosure are effective, fast and accurate, and may solve the problem that the precision of the traditional tomography based on the straight ray theory is low and have a wide application future.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
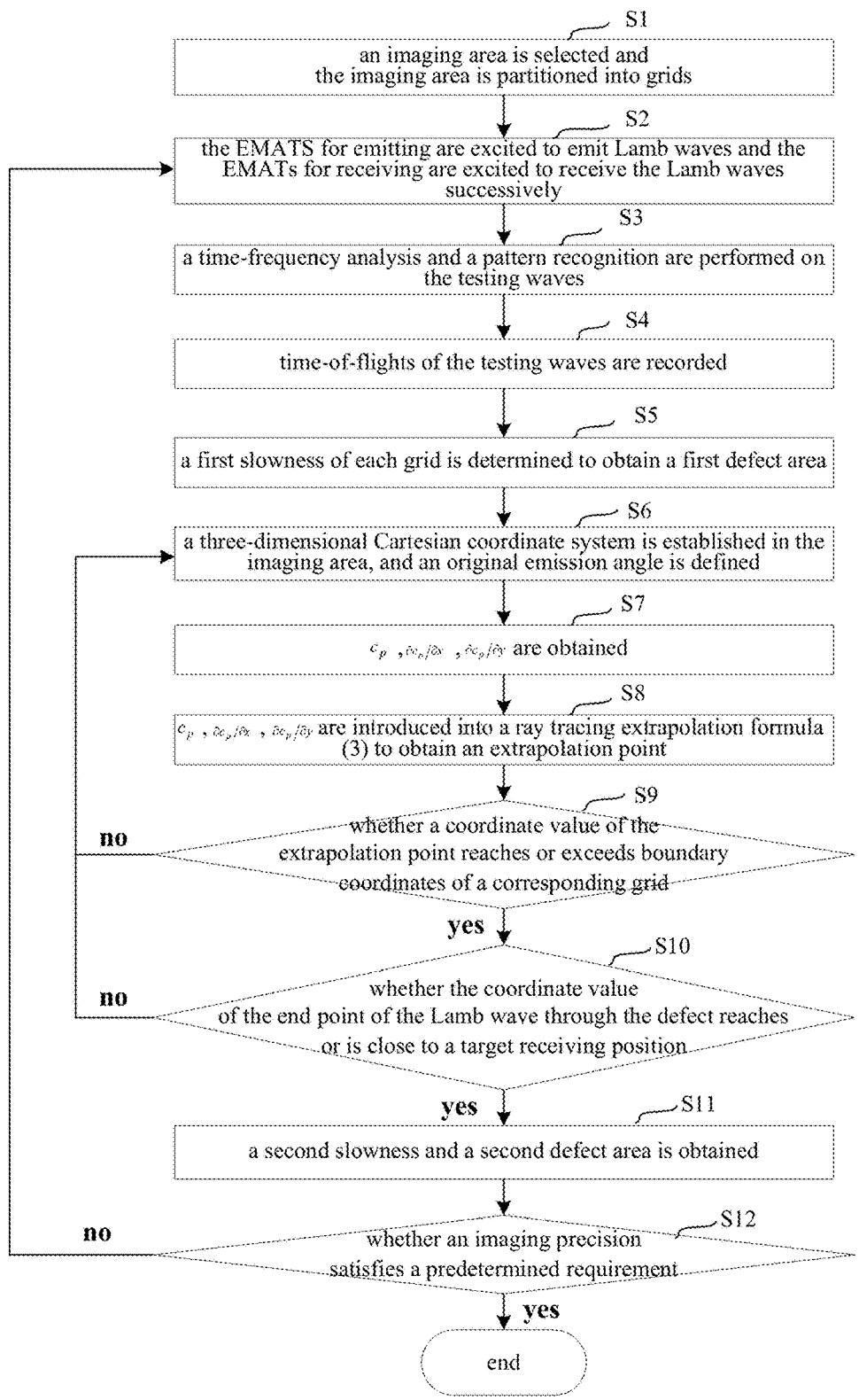
FIG. 1 is a flow chart of a method for testing a defect based on an ultrasonic Lamb wave tomography according to an embodiment of the present disclosure.
Figure 2:
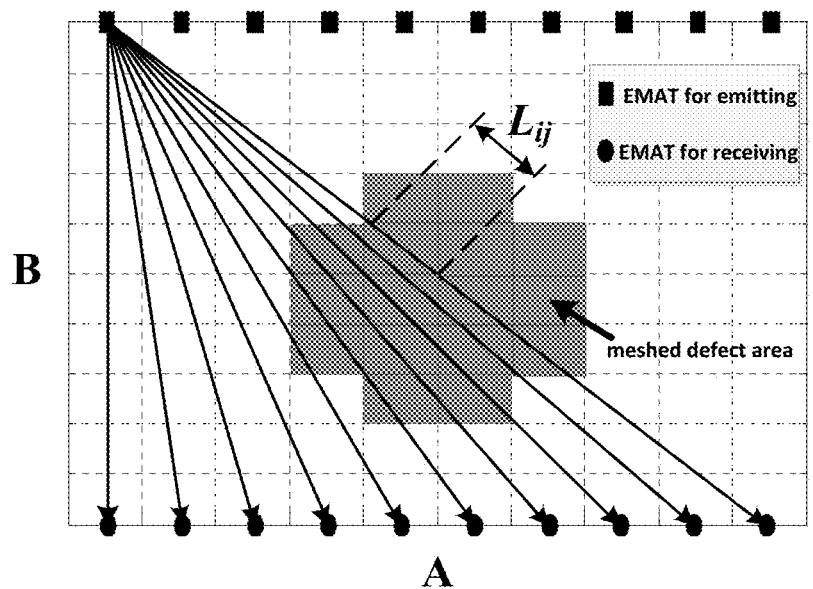
FIG. 2 is schematic diagram of a partition of the imaging area according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

In the specification, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation.

In addition, terms such as "first" and "second" are used herein for purposes of description and are not intended to indicate or imply relative importance or significance. Thus, the feature defined with "first" and "second" may comprise one or more this feature. In the description of the present disclosure, "a plurality of" means two or more than two, unless specified otherwise.

In the description of the present disclosure, it should be understood that, unless specified or limited otherwise, the terms "mounted," "connected," and "coupled" and variations thereof are used broadly and encompass such as mechanical or electrical mountings, connections and couplings, also can be inner mountings, connections and couplings of two components, and further can be direct and indirect mountings, connections, and couplings, which can be understood by those skilled in the art according to the particular embodiment of the present disclosure.

In the description of the present disclosure, a structure in which a first feature is "on" a second feature may include an embodiment in which the first feature directly contacts the second feature, and may also include an embodiment in which an additional feature is formed between the first feature and the second feature so that the first feature does not directly contact the second feature, unless specified otherwise. Furthermore, a first feature "on," "above," or "on top of" a second feature may include an embodiment in which the first feature is right "on," "above," or "on top of" the second feature, and may also include an embodiment in which the first feature is not right "on," "above," or "on top of" the second feature, or just means that the first feature is at a height higher than that of the second feature. While a first feature "beneath," "below," or "on bottom of" a second feature may include an embodiment in which the first feature is right "beneath," "below," or "on bottom of" the second feature, and may also include an embodiment in which the first feature is not right "beneath," "below," or "on bottom of" the second feature, or just means that the first feature is at a height lower than that of the second feature.

The method according to embodiments of the present disclosure is essentially to establish a ray tracing iteration model and to combine the ray tracing iteration model with a time-of-flight cross-hole tomography, such that advantages of the ray tracing iteration model and the time-of-flight cross-hole tomography may be obtained. By iterating, the path of the Lamb waves may be revised to obtain a distribution of a defect. In the following, a detailed description will be explained with reference of embodiments.

In step S1, an imaging area on a material to be tested is selected, and the imaging area is partitioned into $N_1 \times N_2$ grids, in which M electromagnetic acoustic transducers (EMATs) for emitting are set on a first side of the imaging area, and M EMATs for receiving respectively opposite to the M EMATs for emitting are set on a second side of the imaging area, and $N_1$, $N_2$, M are positive integers.

For example, an aluminum sheet to be tested with a thickness in a range of 1-5 mm is provided, and then a rectangular area with an area of A×B on the aluminum sheet to be tested is selected as the imaging area, where A, B are positive integers and are both greater than 30 mm. A standard artificial corrosion defect with a diameter greater than or equal to 30 mm and a depth in a range of 1-5 mm is formed in the imaging area. The imaging area is partitioned into $N_1 \times N_2$ grids (i.e. $N_1 \times N_2$ pixels). The M EMATs for emitting are provided at one side of the imaging area and spaced equally. The M EMATs for receiving respectively opposite to the M EMATs for emitting are provided at other side of the imaging area.

In an embodiment of the present disclosure, a diameter of the EMAT is within a range of 20-80 mm, and a distance of centers of each two adjacent EMATs at the same side is within a range of 20-100 mm.

In step S2, the M EMATs for emitting are excited to emit Lamb waves with a A0 mode in all directions and the M EMATs for receiving are excited to receive the Lamb waves successively, such that M×M testing waves corresponding to M×M Lamb waves are obtained.

In an embodiment of the present disclosure, a radio frequency power amplifier is used to excite the EMATs for emitting. The M EMATs for emitting in an emitting terminal are excited by the radio frequency power amplifier to emit Lamb waves with a A0 mode in all directions, and the M EMATs for receiving in a receiving terminal receive the Lamb waves from the M EMATs for emitting, such that M×M testing waves corresponding to M×M Lamb waves are obtained.

In an embodiment of the present disclosure, an excitation frequency of the radio frequency power amplifier is within a range of 50 kHz to 500 kHz. Each Lamb wave is a Lamb wave with a single A0 mode, and any other mode besides the A0 mode is not contained in the each Lamb wave.

In step S3, a time-frequency analysis and a mode recognition are performed on the M×M testing waves, so as to obtain time-of-flights of the M×M Lamb waves.

In an embodiment of the present disclosure, the time-frequency analysis and the mode recognition are performed on the M×M testing waves using a Pseudo Wigner-Ville Distribution (PWVD).

In step S4, time-of-flights of the M×M Lamb waves are recorded as $T_1 \sim T_{M \times M}$.

Specifically, a time-frequency analysis result of the M×M testing waves is obtained after performing the time-frequency analysis and the mode recognition on the M×M testing waves, in which the time-of-flights $T_1 \sim T_{M \times M}$ of the M×M Lamb waves are included in the time-frequency analysis result of the M×M testing waves.

In step S5, a first slowness (a reciprocal of speed) of each grid is determined according to the time-of-flights $T_1 \sim T_{M \times M}$ and a size of each grid to obtain a first defect area.

Specifically, the first slowness is obtained according to the time-of-flights and a length of each grid.

In an embodiment of the present disclosure, the first slowness and a second slowness described in following description is obtained using a Simultaneous Iterative Reconstruction (SIRT) algorithm formula (1):

$$T_i = \sum_{j=1}^{n} L_{ij} * S_j, \quad (1)$$

$$(i = 1, 2, \ldots, m),$$

where $S_j$ is a slowness of a $j^{th}$ grid, $L_{ij}$ is a length of a $i^{th}$ Lamb wave in the $j^{th}$ grid, is a time-of-flight of the $i^{th}$ Lamb wave, $n = N_1 \times N_2$, and $m = M \times M$.

$L_{ij}$ may be calculated based on the straight ray theory according to the area of the imaging area, the side length of the grid, the number of the EMATs for emitting, the number of the EMATs for receiving, the positions of the EMATs for emitting, the positions of the EMATs for receiving and distances between each two adjacent EMATs on the same side.

The first defect area may be obtained according to the first slowness of each grid. The dispersion property of Lamb wave determines that its velocity changes with the product of the frequency and the aluminum plate thickness. Once the slowness (reciprocal of velocity) distribution of each grid is determined, the velocity distribution of each grid can be obtained. According to the dispersion curve of Lamb wave, the thickness distribution of grids can be obtained based on the velocity. The thickness of areas without defects is the original thickness of the aluminum plate, but the thickness of areas with defects is less than the original thickness. Then the defect area can be determined according to the thickness distribution.

In step S6, a three-dimensional Cartesian coordinate system is established in the imaging area, and an original emission angle is defined, in which a combination of a value in the x axis and a value in the y axis represents a position of a point on a Lamb wave in a two-dimensional surface, and a value in the z axis represents a phase velocity of the point.

In an embodiment of the present disclosure, an original emission angle is within a range of 0-180° is created.

In step S7, for a path of a Lamb wave through the defect, a phase velocity $c_p$ at a point $P(x,y)$ on a forward direction of the Lamb wave through the defect is obtained and $\partial c_p/\partial x$ and $\partial c_p/\partial y$ are calculated according to the phase velocity $c_p$, where x is a coordinate value of the point $P(x,y)$ in a x-direction (i.e. in the x axis), y is a coordinate value of the point $P(x,y)$ in a y-direction (i.e. in the y axis).

Paths of all the Lamb waves through the defect are traced using an extrapolation method.

For a Lamb wave through the defect, a path of the Lamb wave through the defect is traced using an extrapolation method. With regard to the propagation property of the Lamb wave, the phase velocity of the Lamb wave changes with a thickness of the plate if the Lamb wave passes through the defect. Specifically, in an extrapolation area, 16 pixels are obtained with an extrapolation point as a center. And 16 phase velocities corresponding to the Lamb wave with a A0 mode are obtained. And then, the 16 phase velocities are introduced into a two-dimensional cubic spline interpolation (2D-CSI) formula (2) to form 16 linear equations:

$$c_p(x_p, y_p) = \sum_{k=0}^{3} \sum_{l=0}^{3} C_{kl} x_p^k y_p^l, \quad (2)$$

where $x_p$ is a coordinate value of a $p^{th}$ pixel in the x-direction, $y_p$ is a coordinate value of the $p^{th}$ pixel in the y-direction, $c_p(x_p,y_p)$ is a phase velocity corresponding to the $p^{th}$ pixel, $C_{kl}$ are coefficients to be solved, k=0, 1, 2, 3, l=0, 1, 2, 3, p is a positive integer and $1 \leq p \leq 16$, such that $C_{kl}$ are obtained.

A two-dimensional surface fitting is performed on a distribution of the 16 phase velocities. And then $\partial c_p/\partial x$ and $\partial c_p/\partial y$ are calculated.

In step S8, $c_p$, $\partial c_p/\partial x$ and $\partial c_p/\partial y$ are introduced into a ray tracing extrapolation formula (3) to obtain an extrapolation point of the Lamb wave through the defect:

$$y_{k+1} = 2y_k - y_{k-1} - \frac{1}{c_p}\left(\frac{\partial c_p}{\partial x}\frac{(y_k - y_{k-1})}{\Delta x} - \frac{\partial c_p}{\partial y}\right)[(y_k - y_{k-1})^2 + (\Delta x)^2] \quad (3)$$

where $y_k$ is a coordinate value of a first discrete point on the Lamb wave through the defect in the y-direction at a $k^{th}$ step of extrapolation, $y_{k+1}$ is a coordinate value of a second discrete point succeeding the first discrete point on the Lamb wave through the defect in the y-direction at the $k^{th}$ step of extrapolation, $y_{k-1}$ is a coordinate value of a third discrete point preceding the first discrete point on the Lamb wave through the defect in the y-direction at the $k^{th}$ step of extrapolation, $\Delta x$ is a step size, and $\partial y/\partial x = (y_k - y_{k-})/\Delta x$.

In step S9, it is judged whether a coordinate value of the extrapolation point reaches or exceeds boundary coordinates of a corresponding grid, if no, the extrapolation point of the Lamb wave through the defect is used as a new point on the forward direction of the Lamb wave through the defect and steps S6 to S9 is executed, if yes, the coordinate value of the extrapolation point is recorded as a coordinate value $(x_f, y_f)$ of the end point of the Lamb wave through the defect and tracing the Lamb wave through the defect is stopped.

In step S10, it is judged whether the coordinate value $(x_f, y_f)$ of the end point of the Lamb wave through the defect reaches or is close to a target receiving position (i.e. the EMAT for receiving), if yes, a path with a shortest time-of-flight of the Lamb wave through the defect is obtained, if no, the original emission angle is increased or decreased by 2-6° and steps S6-S10 are repeated until the path with the shortest time-of-flight of the Lamb wave through the defect is found.

In step S11, the paths with shortest time-of-flight of all the Lamb waves through the defect are introduced into the Simultaneous Iterative Reconstruction algorithm formula (1) to solve the slowness in each grid to obtain a second slowness of each grid. And then, a second defect area is obtained and a size and a distribution of the second defect area are determined according to a change of a slowness curve.

In step S12, it is judged whether an imaging precision satisfies a predetermined requirement, if no (the imaging precision is low), steps S2-S11 are repeated to obtain a better imaging precision.

Variation 1

In step S1', a square area with a side of 640 mm on an aluminum sheet to be tested with a thickness of 3 mm is selected as an imaging area. A standard artificial corrosion defect with a diameter of 30 mm and a depth of 2 mm is formed in the imaging area. The center of the standard artificial corrosion defect is at a point (320 mm, 460 mm). The imaging area is partitioned into 128×128 grids (128×128 pixels). 14 EMATs for emitting are provided at one side of the imaging area and spaced equally. 14 EMATs for receiving respectively opposite to the 14 EMATs for emitting are provided at other side of the imaging area. A diameter of the EMAT is 30 mm, and a distance of centers of each two adjacent EMATs at the same side is 45.7 mm.

In step S2', a radio frequency power amplifier AG1024 is used to excite the EMATs. A first EMAT for emitting in the emitting terminal is excited to emit the Lamb wave with a A0 mode in all directions, and the 14 EMATs for receiving are excited to receive the Lamb wave successively. An emission frequency of the radio frequency power amplifier is 290 kHz. Each of the other 13 EMATs for emitting in the emitting terminal are excited to emit the Lamb waves with a A0 mode successively. Each Lamb wave is a Lamb wave with a single A0 mode, any other mode besides the A0 mode is not contained in the each Lamb wave.

In step S3', a time-frequency analysis and a mode recognition are performed on 14×14=196 testing waves corresponding to 14×14=196 Lamb waves using a Pseudo Wigner-Ville Distribution.

In step S4', a time-frequency analysis result is obtained and time-of-flights of the 196 testing waves are recorded as $T_1 \sim T_{196}$.

In step S5', a first slowness (a reciprocal of speed) of each grid is determined using a Simultaneous Iterative Reconstruction algorithm formula (1):

$$T_i = \sum_{j=1}^{n} L_{ij} * S_j, \quad (1)$$
$$(i = 1, 2, \ldots, m),$$

where $S_j$ is a slowness of a $j^{th}$ grid, $L_{ij}$ is a length of a $i^{th}$ Lamb wave in the $j^{th}$ grid, is a time-of-flight of the $i^{th}$ Lamb wave, n=128×128=16384, and m=14×14=196.

And the calculated diameter of the first defect area is about 40 mm.

In step S6', a three-dimensional Cartesian coordinate system is established in the imaging area and an original emission angle of 30° is defined.

In step S7', each grid contains 4×4=16 pixels. Paths of all the Lamb waves through the defect are traced using an extrapolation method. In an extrapolation area of a Lamb wave through the defect, 16 pixels are obtained. And 16 corresponding phase velocities are obtained. And then, the 16 phase velocities are introduced into a two-dimensional cubic spline interpolation formula (2) to form 16 linear equations:

$$c_p(x_p, y_p) = \sum_{k=0}^{3} \sum_{l=0}^{3} C_{kl} x_p^k y_p^l. \quad (2)$$

where $x_p$ is a coordinate value of a $p^{th}$ pixel in the x-direction, $y_p$ is a coordinate value of the $p^{th}$ pixel in the y-direction, $c_p(x_p, y_p)$ is a phase velocity corresponding to the $p^{th}$ pixel, $C_{kl}$ are coefficients to be solved, k=0, 1, 2, 3, l=0, 1, 2, 3, p is a positive integer and 1≤p≤16.

A two-dimensional surface fitting is performed on a distribution of the 16 phase velocities. And then $\partial c_p/\partial x$ and $\partial c_p/\partial y$ are calculated.

In step S8', $c_p$, $\partial c_p/\partial x$ and $\partial c_p/\partial y$ obtained in step S6' are introduced into a ray tracing extrapolation formula (3) to obtain an extrapolation point:

$$y_{k+1} = 2y_k - y_{k-1} + \frac{1}{c_p}\left(\frac{\partial c_p}{\partial x}\frac{(y_k - y_{k-1})}{\Delta x} - \frac{\partial c_p}{\partial y}\right)[(y_k - y_{k-1})^2 + (\Delta x)^2] \quad (3)$$

where $y_k$ is a coordinate value of a first discrete point on the Lamb wave through the defect in the y-direction at a $k^{th}$ step of extrapolation, $y_{k+1}$ is a coordinate value of a second discrete point succeeding the first discrete point on the Lamb wave through the defect in the y-direction at the $k^{th}$ step of extrapolation, $y_{k-1}$ is a coordinate value of a third discrete point preceding the first discrete point on the Lamb wave through the defect in the y-direction at the $k^{th}$ step of extrapolation, $\Delta x$ is a step size, and $\partial y/\partial x=(y_k-y_{k-1})/\Delta x$.

In step S9', it is judged whether a coordinate value of the extrapolation point reaches or exceeds boundary coordinates of a corresponding grid, if no, the extrapolation point of the Lamb wave through the defect is used as a new point on the forward direction of the Lamb wave through the defect and steps S6' to S9' is executed, if yes, the coordinate value of the extrapolation point is recorded as a coordinate value $(x_f, y_f)$ of the end point of the Lamb wave through the defect and tracing the Lamb wave through the defect is stopped.

In step S10', it is judged whether the coordinate value $(x_f, y_f)$ of the end point of the Lamb wave through the defect reaches or is close to a target receiving position (i.e. the EMAT for receiving), if yes, a path with a shortest time-of-flight of the Lamb wave through the defect is obtained, if no, the original emission angle is increased or decreased by 3° and steps S6'-S10' are repeated until the path with the shortest time-of-flight of the Lamb wave through the defect is found.

In step S11', the paths with shortest time-of-flight of all the Lamb waves through the defect are found are introduced into the Simultaneous Iterative Reconstruction algorithm formula (1) to solve the slowness in each grid to obtain a second slowness of each grid. And then, a second defect area is obtained and a size and a distribution of the second defect area are determined according to a change of a slowness curve.

Steps S2'-S11' are repeated to obtain a better imaging precision. Generally, if the error of each of the length, width and depth of the defect is less than 10%, the imaging precision is considered to satisfy the predetermined requirement. In this embodiment, the calculated diameter of the second defect area is 32 mm, which corresponds to the actual value. The error is less than 10%.

Figure 3:
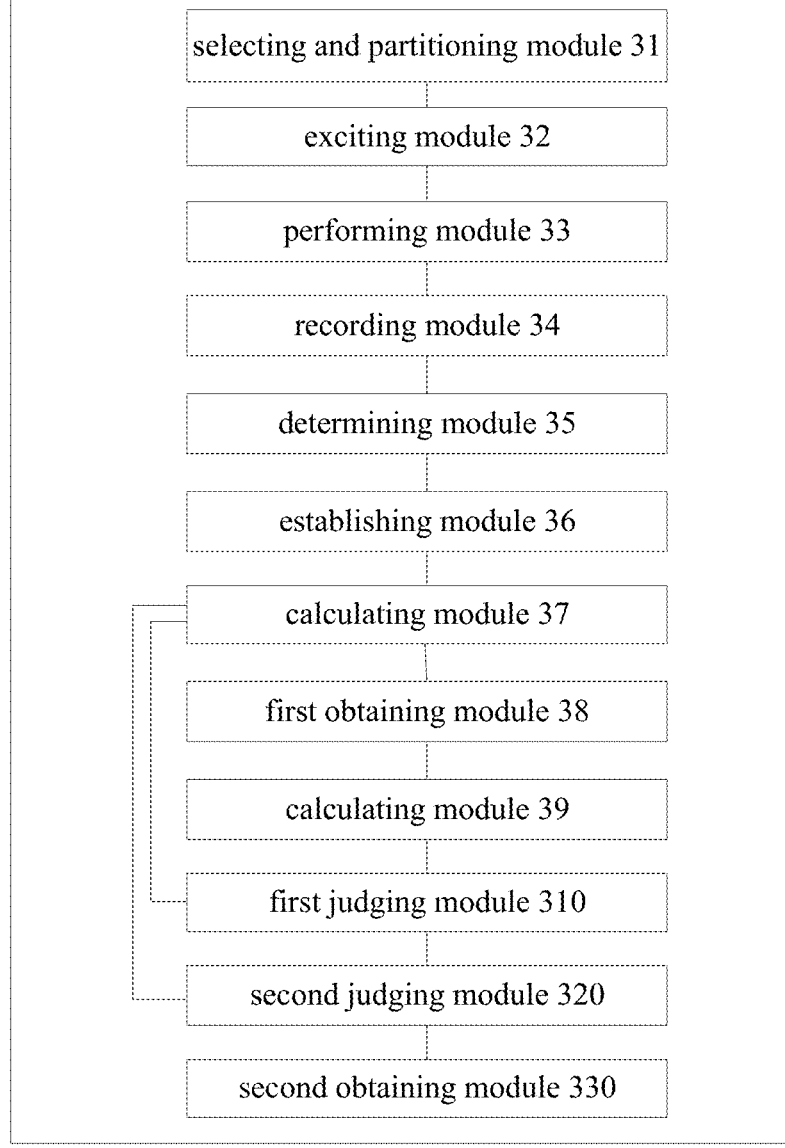
FIG. 3 is a block diagram of a device for testing a defect based on an ultrasonic Lamb wave tomography according to an embodiment of the present disclosure.

FIG. 3 is a block diagram of a device for testing a defect based on an ultrasonic Lamb wave tomography according to an embodiment of the present disclosure. As shown in FIG. 3, the device 30 for testing a defect based on an ultrasonic Lamb wave tomography includes: a non-transitory computer-readable medium comprising computer-executable instructions stored thereon; and an instruction execution system, which is configured by the instructions to implement at least one of following modules:

a selecting and partitioning module 31, configured to select an imaging area on a material to be tested and partition the imaging area into $N_1 \times N_2$ grids, in which M EMATs for emitting are set on a first side of the imaging area, M EMATs for receiving are set respectively opposite to the M EMATs for emitting on a second side of the imaging area, and $N_1$, $N_2$, M are positive integers.

an exciting module 32, configured to excite the M EMATs for emitting to emit Lamb waves with a A0 mode in all directions and the M EMATs for receiving to receive the Lamb waves successively, such that M×M testing waves are obtained.

a performing module 33, configured to perform a time-frequency analysis and a mode recognition on the M×M testing waves, so as to obtain time-of-flights of the M×M Lamb waves.

a recording module 34, configured to record the time-of-flights of the M×M Lamb waves.

a determining module 35, configured to determine a first slowness of each grid according to the time-of-flights and a size of each grid to obtain a first defect area.

an establishing module 36, configured to establish a three-dimensional Cartesian coordinate system in the imaging area and define an original emission angle.

a first obtaining module 37, for a path of a Lamb wave through the defect, configured to obtain a phase velocity $c_p$ at a point P(x,y) on a forward direction of the path of the Lamb wave through the defect, and calculate $\partial c_p/\partial x$ and $\partial c_p/\partial y$ according to the phase velocity $c_p$, where x is a coordinate value of the point P(x,y) in a x-direction, y is a coordinate value of the point P(x,y) in a y-direction.

In an embodiment of the present disclosure, the first obtaining module 37 is further configured to:

obtain 16 pixels with the extradition point used as a center;

obtain 16 phase velocities corresponding to the 16 pixels;

introduce the 16 phase velocities respectively into a formula (2) to perform a two-dimensional surface fitting on a distribution of the phase velocities:

$$c_p(x_p, y_p) = \sum_{k=0}^{3} \sum_{l=0}^{3} C_{kl} x_p^k y_p^l, \quad (2)$$

where $x_p$ is a coordinate value of a $p^{th}$ pixel in the x-direction, $y_p$ is a coordinate value of the $p^{th}$ pixel in the y-direction, $c_p(x_p,y_p)$ is a phase velocity corresponding to the $p^{th}$ pixel, $c_{kl}$ are coefficients to be obtained, k=0, 1, 2, 3, l=0, 1, 2, 3, p is a positive integer and 1≤p≤16, such that $C_{kl}$ are obtained;

calculate $\partial c_p/\partial x$ and $\partial c_p/\partial y$ according to $C_{kl}$.

a calculating module 38, configured to calculate an extrapolation point of the Lamb wave through the defect by introducing $c_p$, $\partial c_p/\partial x$ and $\partial c_p/\partial y$ into an extrapolation formula.

a first judging module 39, configured to judge whether a coordinate value of the extrapolation point reaches or exceeds boundary coordinates of a corresponding grid, if no, use the extrapolation point of the Lamb wave through the defect as a new point on the forward direction of the Lamb wave through the defect and make the establishing module 36, the first obtaining module 37, the calculating module 38 and the first judging module 39 to work again, and if yes, record the coordinate value of the extrapolation point as a coordinate value of an end point of the Lamb wave through the defect.

a second judging module 310, configured to judge whether the coordinate value of the end point of the Lamb wave through the defect reaches or is close to the electromagnetic acoustic transducers for receiving, if yes, obtain a path with a shortest time-of-flight of the Lamb wave through the defect, and if no, change the original emission angle and make the establishing module 36, the first obtaining module 37, the calculating module 38, the first judging module 39 and the second judging module 310 to work together until the path with the shortest time-of-flight of the Lamb wave through the first defect area is found.

a second obtaining module 320, configured to obtain a second slowness of each grid according to the time-frequency analysis result and the shortest time-of-flights and a change of a slowness curve in the defect to obtain a second defect area and to determine a size and a distribution of the second defect area.

In some embodiments, a diameter of the EMAT is within a range of 20 mm to 80 mm, a distance between centers of each two adjacent EMATs at the same side is within a range of 20 mm to 100 mm.

In some embodiments, the M EMATs for emitting are excited by a radio frequency power amplifier, in which an excitation frequency of the radio frequency power amplifier is within a range of 50 kHz to 500 kHz.

In some embodiments, the first or the second slowness of each grid is determined according to formula (1):

$$T_i = \sum_{j=1}^{n} L_{ij} * S_j, \quad (1)$$

$$(i = 1, 2, \ldots, m),$$

where $S_j$ is a slowness of a $j^{th}$ grid, $L_{ij}$ is a length of a $i^{th}$ Lamb wave in the $j^{th}$ grid, is a time-of-flight of the $i^{th}$ Lamb wave, n=$N_1 \times N_2$, and m=M×M.

In some embodiments, the original emission angle is within a range of 0~180° and the second judging module is configured to change the original emission angle by increasing or decreasing the original emission angle by 2~6°.

In some embodiments, the extrapolation formula is expressed as formula (3):

$$y_{k+1} = 2y_k - y_{k-1} + \frac{1}{c_p}\left(\frac{\partial c_p}{\partial x}\frac{(y_k - y_{k-1})}{\Delta x} - \frac{\partial c_p}{\partial y}\right)[(y_k - y_{k-1})^2 + (\Delta x)^2] \quad (3)$$

where $y_k$ is a coordinate value of a first discrete point on the Lamb wave through the defect in a y-direction at a $k^{th}$ step of extrapolation, $y_{k+1}$ is a coordinate value of a second discrete point succeeding the first discrete point on the Lamb wave through the defect in the y-direction at the $k^{th}$ step of extrapolation, $y_{k-1}$ is a coordinate value of a third discrete point preceding the first discrete point on the Lamb wave through the defect in the y-direction at the $k^{th}$ step of extrapolation, $\Delta x$ is a step size, and $\partial y/\partial x=(y_k-y_{k-1})/\Delta x$.

In some embodiments, the device 30 for testing a defect based on an ultrasonic Lamb wave tomography further includes a third judging module, configured to judge whether an imaging precision corresponds to a predetermined requirement.

It will be understood that, the flow chart or any process or method described herein in other manners may represent a module, segment, or portion of code that comprises one or more executable instructions to implement the specified logic function(s) or that comprises one or more executable instructions of the steps of the progress. Although the flow chart shows a specific order of execution, it is understood that the order of execution may differ from that which is depicted. For example, the order of execution of two or more boxes may be scrambled relative to the order shown.

Reference throughout this specification to "an embodiment," "some embodiments," "one embodiment," "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for testing a defect based on an ultrasonic Lamb wave tomography, comprising following acts performed by a computer:

S1, selecting an imaging area on a material to be tested, and partitioning the imaging area into $N_1 \times N_2$ grids, wherein M electromagnetic acoustic transducers for emitting are set on a first side of the imaging area, M electromagnetic acoustic transducers for receiving are set respectively opposite to the M electromagnetic acoustic transducers for emitting on a second side of the imaging area, and $N_1$, $N_2$, M are positive integers;

S2, exciting the M electromagnetic acoustic transducers for emitting to emit Lamb waves with a A0 mode in all directions and the M electromagnetic acoustic transducers for receiving to receive the Lamb waves successively, such that M×M testing waves corresponding to M×M Lamb waves are obtained;

S3, performing a time-frequency analysis and a mode recognition on the M×M testing waves, so as to obtain time-of-flights of the M×M Lamb waves;

S4, recording the time-of-flights of the M×M Lamb waves;

S5, determining a first slowness of each grid according to the time-of-flights and a size of each grid to obtain a first defect area;

S6, establishing a three-dimensional Cartesian coordinate system in the imaging area, and defining an original emission angle;

S7, for a path of a Lamb wave through the defect, obtaining a phase velocity $c_p$ at a point P(x,y) on a forward direction of the Lamb wave through the defect and calculating $\partial c_p/\partial x$ and $\partial c_p/\partial y$ according to the phase velocity $c_p$, where x is a coordinate value of the point P(x,y) in a x-direction, y is a coordinate value of the point P(x,y) in a y-direction;

S8, calculating an extrapolation point of the Lamb wave through the defect by introducing $c_p$, $\partial c_p/\partial x$ and $\partial c_p/\partial y$ into an extrapolation formula;

S9, judging whether a coordinate value of the extrapolation point reaches or exceeds boundary coordinates of a corresponding grid, if no, using the extrapolation point of the Lamb wave through the defect as a new point on the forward direction of the Lamb wave through the defect and executing steps S6-S9, if yes, recording the coordinate value of the extrapolation point as a coordinate value of the end point of the Lamb wave through the defect;

S10, judging whether the coordinate value of the end point of the Lamb wave through the defect reaches or is close to the electromagnetic acoustic transducers for receiving, if yes, obtaining a path with a shortest time-of-flight of the Lamb wave through the defect, if no, changing the original emission angle and executing steps S6-S10 until the path with the shortest time-of-flight of the Lamb wave through the first defect area is found;

S11, obtaining a second slowness of each grid according to the time-frequency analysis result and the shortest time-of-flight and a change of a slowness curve in the defect to obtain a second defect area and to determine a size and a distribution of the second defect area.

2. The method according to claim 1, wherein a diameter of the electromagnetic acoustic transducer is within a range of 20 mm to 80 mm, a distance between centers of each two adjacent electromagnetic acoustic transducers at the same side is within a range of 20 mm to 100 mm.

3. The method according to claim 1, wherein the M electromagnetic acoustic transducers for emitting are excited by a radio frequency power amplifier, in which an excitation frequency of the radio frequency power amplifier is within a range of 50 kHz to 500 kHz.

4. The method according to claim 1, wherein the Lamb wave emitted by the electromagnetic acoustic transducer for emitting is a Lamb wave with a single A0 mode.

5. The method according to claim 1, wherein the first or the second slowness of each grid is determined according to formula (1):

$$T_i = \sum_{j=1}^{n} L_{ij} * S_j, \qquad (1)$$

$$(i = 1, 2, \ldots, m),$$

where $S_j$ is a slowness of a $j^{th}$ grid, $L_{ij}$ is a length of a $i^{th}$ Lamb wave in the $j^{th}$ grid, $T_i$ is a time-of-flight of the $i^{th}$ Lamb wave, $n = N_1 \times N_2$, and $m = M \times M$.

6. The method according to claim 1, wherein the original emission angle is within a range of 0~180°.

7. The method according to claim 1, wherein obtaining a phase velocity $c_p$ at a point P(x,y) on a forward direction of the Lamb wave through the defect and calculating $\partial c_p/\partial x$ and $\partial c_p/\partial y$ according to the phase velocity $c_p$ comprises:

obtaining 16 pixels with the extradition point used as a center;

obtaining 16 phase velocities corresponding to the 16 pixels;

introducing the 16 phase velocities respectively into a formula (2) to perform a two-dimensional surface fitting on a distribution of the phase velocities:

$$c_p(x_p, y_p) = \sum_{k=0}^{3} \sum_{l=0}^{3} C_{kl} x_p^k y_p^l, \qquad (2)$$

where $x_p$ is a coordinate value of a $p^{th}$ pixel in the x-direction, $y_p$ is a coordinate value of the $p^{th}$ pixel in the y-direction, $c_p(x_p,y_p)$ is a phase velocity corresponding to the $p^{th}$ pixel, $C_{kl}$ are coefficients to be solved, k=0, 1, 2, 3, l=0, 1, 2, 3, p is a positive integer and $1 \leq p \leq 16$, such that $C_{kl}$, are obtained;

calculating $\partial c_p/\partial x$ and $\partial c_p/\partial y$ according to $C_{kl}$.

8. The method according to claim 1, wherein the extrapolation formula is expressed as formula (3):

$$y_{k+1} = 2y_k - y_{k-1} + \frac{1}{c_p}\left(\frac{\partial c_p}{\partial x}\frac{(y_k - y_{k-1})}{\Delta x} - \frac{\partial c_p}{\partial y}\right)[(y_k - y_{k-1})^2 + (\Delta x)^2] \quad (3)$$

where $y_k$ is a coordinate value of a first discrete point on the Lamb wave through the defect in a y-direction at a $k^{th}$ step of extrapolation, $y_{k+1}$ is a coordinate value of a second discrete point succeeding the first discrete point on the Lamb wave through the defect in the y-direction at the $k^{th}$ step of extrapolation, $y_{k+1}$ is a coordinate value of a third discrete point preceding the first discrete point on the Lamb wave through the defect in the y-direction at the $k^{th}$ step of extrapolation, $\Delta x$ is a step size, and $\partial y/\partial x = (y_k - y_{k-1})/\Delta x$.

9. The method according to claim 1, wherein changing the original emission angle comprises:

increasing or decreasing the original emission angle by 2~6°.

10. The method according to claim 1, further comprising:

S12, judging whether an imaging precision satisfies a predetermined requirement, and if no, repeating steps S2-S11.

\* \* \* \* \*